(12) United States Patent
Jans et al.

(10) Patent No.: US 10,881,363 B2
(45) Date of Patent: Jan. 5, 2021

(54) IMAGING SYSTEM WITH DYNAMIC BEAM SIZE LIMITATION

(71) Applicant: KONINKLIJKE PHILIPS N.V., Eindhoven (NL)

(72) Inventors: Johannes Cornelis Jans, Maasbracht (NL); Rob Van Loon, Eindhoven (NL); Niels Methorst, Best (NL); Pascal Wolkotte, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/337,432

(22) PCT Filed: Sep. 29, 2017

(86) PCT No.: PCT/EP2017/074917
§ 371 (c)(1),
(2) Date: Mar. 28, 2019

(87) PCT Pub. No.: WO2018/060507
PCT Pub. Date: Apr. 5, 2018

(65) Prior Publication Data
US 2019/0231283 A1    Aug. 1, 2019

(30) Foreign Application Priority Data

Sep. 29, 2016  (EP) .................................... 16191439

(51) Int. Cl.
*H05G 1/52* (2006.01)
*G21K 1/00* (2006.01)
(Continued)

(52) U.S. Cl.
CPC .................. *A61B 6/08* (2013.01); *A61B 6/06* (2013.01); *A61B 6/4441* (2013.01); *A61B 6/587* (2013.01); *A61B 6/542* (2013.01); *A61B 6/582* (2013.01)

(58) Field of Classification Search
CPC ............ A61K 41/0042; A61K 41/0057; A61K 41/00; A61K 41/008; A61K 41/17;
(Continued)

(56) References Cited

U.S. PATENT DOCUMENTS

| | | | |
|---|---|---|---|
| 6,106,152 A | 8/2000 | Thunberg | |
| 6,370,218 B1 * | 4/2002 | Toth | A61B 6/032 378/113 |

(Continued)

FOREIGN PATENT DOCUMENTS

| | | |
|---|---|---|
| EP | 1065670 A2 | 1/2001 |
| WO | 2004006770 A2 | 1/2004 |

(Continued)

OTHER PUBLICATIONS

"Medical electrical equipment—Part 2-43: Particular requirements for the basic safety and essential performance of X-ray equipment for interventional procedures", NSAI Standards, IEC 60601-2-43, 2010.

*Primary Examiner* — Irakli Kiknadze

(57) ABSTRACT

An imaging system (10) comprises a beam source (20), a detector unit (30), a beam limiting unit (40), and a control unit (50). The beam source (20) generates a beam (22) and projects it onto the detector unit (30), thus generating a radiated field (32) being limited by the beam limiting unit (40). The detector unit (30) provides image data as a result of the beam (22). The control unit (50) is configured to provide image data of a desired region of an object (60) by selecting a predetermined image field (34) of the detector unit. The control unit (50) is configured to determine a (Continued)

correction factor for a relative position and/or a relative orientation of the image field (34) with respect to the radiated field based on an orientation of the imaging system and to control the beam limiting unit as to reduce the cross-sectional area of the beam.

14 Claims, 2 Drawing Sheets

(51) Int. Cl.
*A61B 6/08* (2006.01)
*A61B 6/06* (2006.01)
*A61B 6/00* (2006.01)

(58) Field of Classification Search
CPC ........ A61K 9/0009; A61B 6/032; A61B 6/14; A61B 6/542; A61B 6/548; A61B 6/027; A61B 6/022; A61B 6/06; A61B 6/4233; A61B 6/4464; A61B 6/587; A61B 6/4405; A61B 6/08; A61B 6/469; A61B 6/4441; A61B 6/467; A61B 6/547; A61B 6/588; A61B 6/4007; A61B 6/4021; A61B 6/4283; A61B 6/4411; A61B 6/582; A61B 6/487; A61B 6/503; A61B 6/5241; A61B 6/5288; A61B 6/585; A61B 6/4291; A61B 2562/04; A61B 5/0059; A61B 5/0075; A61B 5/0091; A61B 5/1455; A61B 5/4244; A61B 5/4848; A61B 6/583; A61B 6/405; A61B 6/482; A61B 6/0487; A61B 6/4035; A61B 6/488; A61B 6/0457; A61B 6/541; A61B 6/4085; A61B 6/4241; H04N 5/32; H04N 5/3572; A61N 2005/1034; A61N 5/1031; A61N 5/1038; A61N 2005/1008; A61N 2005/1076; A61N 2005/109; A61N 2005/1095; A61N 5/10; A61N 5/1001; A61N 5/1007; A61N 5/1042; A61N 5/1075; A61N 2005/1059; A61N 5/1049; A61N 5/1067; G01T 1/2002; G01T 1/2006; G01T 1/2018; G01T 1/208; G01T 7/005; G01T 1/2012; G01T 1/1642; G01T 1/247; G01T 1/2008; G01T 1/29; G16H 20/40; G16H 30/20; H05G 1/26; H05G 1/60; H05G 1/46; G01N 2223/419; G01N 23/046; G01N 23/04; G21K 1/04
USPC ................................................. 378/113, 145
See application file for complete search history.

(56) References Cited

U.S. PATENT DOCUMENTS

| 6,937,693 | B2 * | 8/2005 | Svatos | A61N 5/103 |
| | | | | 378/108 |
| 2004/0015077 | A1 | 1/2004 | Sati | |
| 2004/0127789 | A1 | 7/2004 | Ogawa | |
| 2004/0260103 | A1 | 12/2004 | Matusz et al. | |
| 2008/0260103 | A1 | 10/2008 | Zaiki | |
| 2013/0243155 | A1 | 9/2013 | Ryu | |
| 2016/0117823 | A1 | 4/2016 | Isaacs | |
| 2016/0166230 | A1 | 6/2016 | Kim | |

FOREIGN PATENT DOCUMENTS

| WO | 2015051468 A1 | 4/2015 |
| WO | 2016097174 A1 | 6/2016 |

* cited by examiner

IMAGING SYSTEM WITH DYNAMIC BEAM SIZE LIMITATION

CROSS-REFERENCE TO PRIOR APPLICATIONS

This application is the U.S. National Phase application under 35 U.S.C. § 371 of International Application No. PCT/EP2017/074917, filed on Sep. 29, 2017, which claims the benefit of European Patent Application No. 16191439.5, filed on Sep. 29, 2016. These applications are hereby incorporated by reference herein.

FIELD OF THE INVENTION

The present invention relates to an imaging system, a method for controlling an imaging system, a computer program element for controlling an imaging system, and a computer-readable medium having stored such a computer program element.

BACKGROUND OF THE INVENTION

An imaging system typically comprises a beam source, a detector unit, and an arm holding the beam source and the detector unit. For example, the beam source may be an X-ray source and the arm may be a C-arm, wherein the beam source is mounted to a first end of the C-arm and the detector unit is mounted to a second end of the C-arm. Such an imaging system may be generally referred to as a C-arm imaging device.

The beam source emits rays, which are passed through an object, for example a patient's body. On the other side of the C-arm, the detector unit detects the rays and converts the received photons into an image signal. As to change the perspective or the position the image is being taken from, the C-arm can be rotated to multiple positions such that the rays pass the interested portion of the object at a desired or determined angle.

Images captured with such an imaging system may exhibit distortions due to several sources. One possible source of distortion is gravity and the mass of the imaging system components, namely the beam source, the detector unit and the C-arm. Due to the fact that the C-arm is rotated about the measuring field, the force of gravity may deform the C-arm, resulting in a change of the relative position of the beam source and the detector unit. Such deformations may vary with changes in the orientation of the C-arm, resulting in radial and/or rotational distortions or misalignments of the image produced by the detector unit.

As a result of this distortion or misalignment, the size of the radiated beam must be adjusted in a manner that the image is captured such that it is located in each case within the beam. In other words, the cross section of the beam must be larger than the cross section of the image such that the image is not misaligned (for example shifted or laterally offset) with respect to the beam to an undesired extent due to bending of the C-arm.

In order to ensure that the image field is located within the beam (or: radiated field), the cross-section and size of the beam is determined in consideration of possible maximum distortion or misalignment for several image field sizes and/or shapes. In particular, the radiated field is larger than the image field and comprises a margin section going beyond the margin of the image field. As a consequence of the radiation field being larger than the image field, the complete radiation dose is also larger than the radiation dose needed in the optimal case where the image field is of the same size as the radiation field.

WO 2004/006770 A2 describes a C-arm imaging device, method, and system with position determination means for determining the position of an imaging source and an imaging apparatus, and means for determining a local gravity vector. Imaging source focal point displacement due to bending of the C-arm is described.

SUMMARY OF THE INVENTION

In view of the previous explanations, there may be a need to provide an improved beam size limitation for reducing the radiation exposure during operation of an imaging system.

This need is addressed by the subject-matter of the independent claims, wherein further embodiments are incorporated in the dependent claims. It should be noted that the following described aspects of the invention apply also for the method, the computer program element and the computer-readable medium, at least in an analogous manner.

According to an aspect of the invention, an imaging system is provided. The imaging system comprises a beam source, a detector unit, a beam limiting unit, and a control unit. The beam source is configured to generate a beam and to project the beam onto the detector unit such that a radiated field is projected onto the detector unit. The beam limiting unit is configured to limit the radiated field, in particular the size and the shape of the radiated field. The detector unit is configured to provide image data as a result of the beam being projected onto the detector unit. The control unit is configured to provide image data as to generate an image of a desired region of an object being arranged between the beam source and the detector unit by selecting a predetermined image field of the detector unit. The control unit is further configured to determine a correction factor for a position and/or an orientation of the image field with respect to the radiated field based on an orientation of the imaging system and to apply the correction factor to the position and/or the orientation of the image field with respect to the radiated field such that the image field is repositioned and/or oriented with respect to the radiated field. The control unit is further configured to control the beam limiting unit as to reduce the cross-sectional area of the beam projected to the detection unit based on the orientation of the imaging system.

The imaging system as described herein is configured to reposition and/or adapt the orientation of the image field with respect to the radiated field depending on the position of the beam source with respect to the detector unit and the orientation of these components with respect to each other. The orientation of the beam source with respect to the detector unit may be the angular orientation of a (virtual) connection line between the beam source and the detector unit with respect to the force of gravity. Depending on this angular orientation, the loads resulting from the force of gravity varies and bending forces of different extent and directions are applied to the imaging system and its components. As a result, the focus of the beam may be offset, misaligned, or displaced with respect to the detector unit, i.e., the image field is offset within the radiated field. It should be noted that the terms "offset", "misaligned", and "displaced" are used as synonyms in the context of this description and with reference to the changes of the relative position and/or orientation of the image field with respect to the radiated field.

Subsequently, the position and/or orientation of the image field is adapted with respect to the radiated field based on the orientation of the beam source and the detector unit. It is noted that this repositioning is a relative repositioning and may be done, for example, by moving, resizing, or reshaping the image field and/or by moving, resizing, or reshaping the radiated field. For example, the image field may be centered within the radiated field. In other words, the image field is shifted with respect to the radiated field. Alternatively or additionally, the radiated field may be resized and reshaped such that the image field changes the relative position and/or orientation within the radiated field.

Size and shape of the image field may be defined by identification of an area or field at the detector unit to be read out. Thus, shifting of the image field within the radiated field may happen by selecting an alternative area or field on the surface of the detector unit which alternative area or field corresponds to the repositioned image field.

After having repositioned the image field within the radiated field, the size of the radiated field is reduced as to reduce the entire radiation dose. However, it is also possible that the reduction of the size of the radiated field is done at the same time with the repositioning of the image field. For example, a correction factor for the position of the image field and a correction factor for the opening size and/or shape of the beam limiting unit may be assigned to multiple angles of orientation and/or positions of the imaging system such that both correction factors can be applied to the imaging system and its components at the same time.

According to another aspect of the invention, a method for operating an imaging system is provided, in particular for capturing an image by using the imaging system. The method comprises the following steps:
a) determining an orientation of the imaging system;
b) determining a correction factor to be applied to an image field with respect to a radiated field based on the orientation of the imaging system;
c) applying the correction factor to the image field and repositioning the image field and/or adapting the orientation of the image field with respect to the radiated field;
d) reducing the cross-sectional area of the radiated field unit based on the orientation of the imaging system;
e) capturing an image of the image field.

It is understood that, without repeating here all the explanations, examples, features and/or advantages provided with respect to the imaging system, the method of the invention is intended to be configured to carry out the method steps for which the imaging system is configured to. Thus, all the above provided examples, explanations, features and/or advantages, although provided previously with reference to the image system, are also to be intended as being provided in an analogous manner for the method of the invention.

According to another aspect of the invention, a computer program element for controlling an imaging system of the invention is provided, which, when being executed by a control unit, is adapted to carry out the steps of the method described above.

According to another aspect of the invention, a computer-readable medium having stored thereon the program element is provided, which, when being executed by a control unit, is adapted to carry out the steps of the method described above.

According to an aspect of the present invention, the relative position and orientation of an image field with respect to a radiated field is adapted or adjusted. This relative repositioning re-orientation may be done by repositioning and/or re-orienting the image field and/or by repositioning and/or re-orienting the radiated field. For example, repositioning of the image field may be done such that a margin area of the radiated field going beyond the image field is substantially of the same width along the circumference of the radiated field. Preferably, the image field is centered within the radiated field. Subsequently, the size of the radiated field may be reduced such that the radiation dose for capturing the image is reduced as well. Reducing the size of the radiated field may be done by adapting an opening of the beam limiting unit, for example by reducing the opening angle of a collimator. Thus, the radiation dose is reduced and, in particular, the ratio of the radiation dose used for capturing the image with regard to the total radiation dose is increased. In other words, the ratio of the size of the image field with respect to the size of the radiated field is increased.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

In the following, the invention is exemplarily described as being used in the context of the apparatus for determining a fractional flow reserve. But the invention can also be used in the context of the method for determining a fractional flow reserve. Thus, all the following examples and/or explanations may also be intended as being implemented by the method of the invention.

Figure 1:
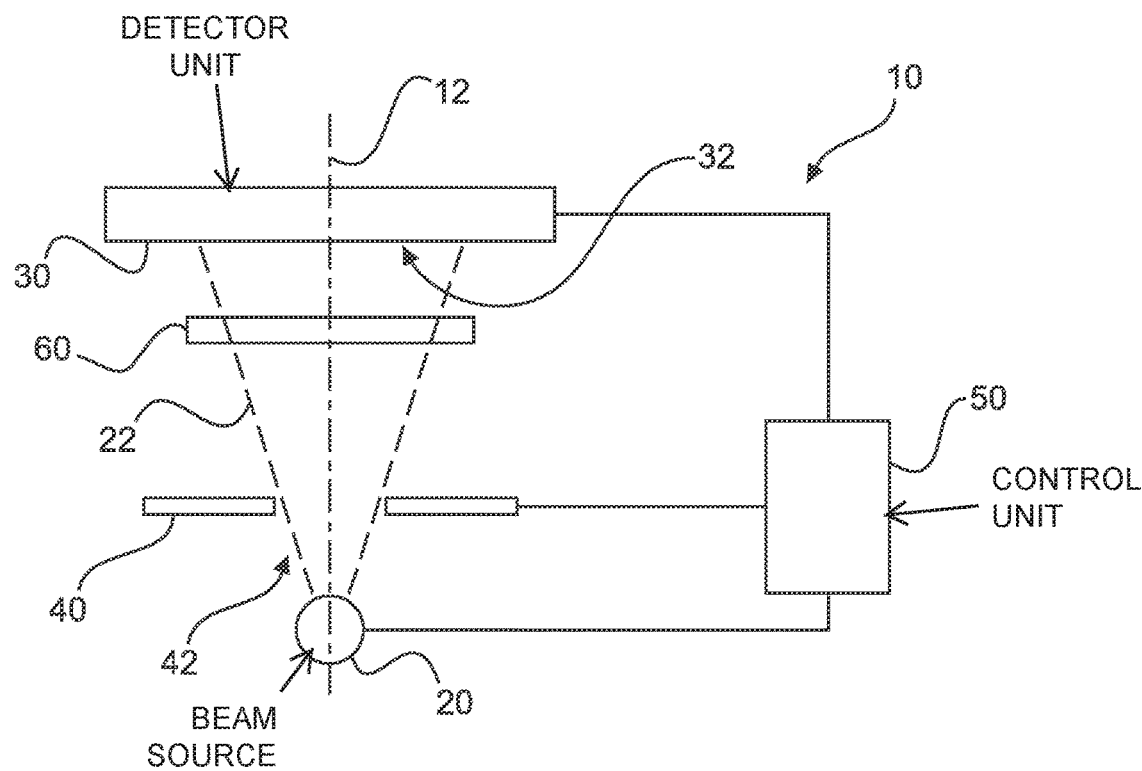
FIG. 1 schematically illustrates an exemplary embodiment of an imaging system.
Figure 2:
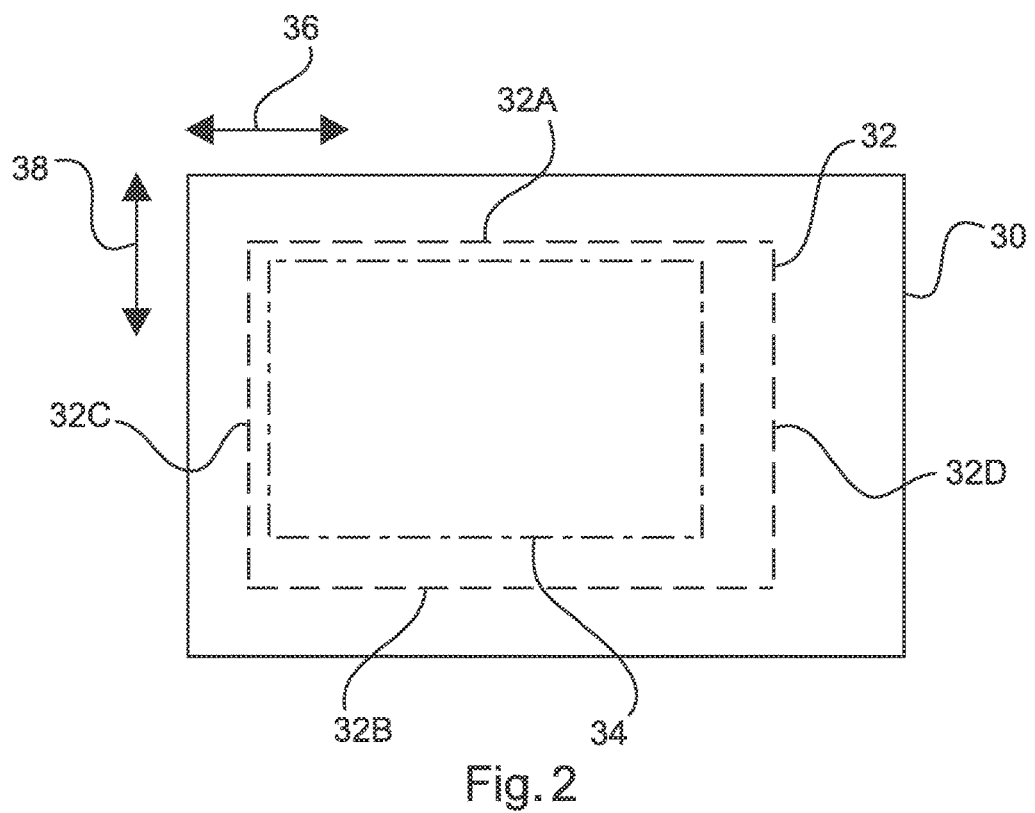
FIG. 2 schematically illustrates an exemplary embodiment of a detector unit of an imaging system.

FIG. 1 schematically illustrates an imaging system 10. The imaging system comprises a beam source 20, a detector unit 30, a beam limiting unit 40, and a control unit 50. The beam source 20 is configured to generate a beam 22 and to project the beam onto the detector unit 30, in particular onto a surface of the detector unit, such that a radiated field 32 is projected onto said surface of the detector unit. The beam limiting unit 40 is configured to limit the radiated field 32. The beam limiting unit 40 comprises an opening 42 and may be a collimator with an adjustable size of the opening. The detector unit 30 is configured to provide image data as a result of the beam 22 being projected onto the detector unit. The control unit 50 is configured to provide image data as to generate an image of a desired region of an object 60 being arranged between the beam source and the detector unit by selecting a predetermined image field 34 of the detector unit, as shown in FIG. 2.

The control unit 50 is further configured to determine a correction factor for a position and/or an orientation of the image field 34 based on an orientation of the imaging system and to apply the correction factor to the position and/or the orientation of the image field 34 within the radiated field 32 such that the image field 34 is repositioned and/or oriented within the radiated field 32. The control unit is further configured to control the beam limiting unit 40 as to reduce the cross-sectional area of the beam projected to the detection unit after repositioning of the image field. In other words, the opening 42 of the beam limiting unit defines the size and shape of the radiated field 32.

The cross sectional area of the beam may be reshaped by individually controlling one or multiple beam shutters of the beam limiting device, wherein each beam shutter is arranged to define and limit one edge of the radiated field.

An object 60 may be arranged between the beam source 20 and the detector unit 30. The beam, which is an X-ray beam, for example, projects through the object 60 onto the surface of the detector unit 30, such that the image data allow conclusions to the composition and condition of the object.

A central axis 12 indicates a center of the beam 22. The imaging system may comprise a C-arm holding the beam source 20 and the detector unit 40. Depending on the position and orientation of the C-arm (and, therefore, depending on the position and orientation of the beam source and the detector unit with respect to each other), the projection of the beam onto the detector unit may change due to the force of gravity acting on the beam source and the detector unit. The gravitational force may result in bending or applied bending forces and/or plastic strain and may cause plastic deformation of the C-arm. Due to this deformation, the radiated field may be repositioned on the surface of the detector unit.

In order not to capture an image out of the boundaries of the radiated field, the radiated field 32 must be larger than the desired image field 34, see FIG. 2, so that the image field 34 is located within the radiated field 32 under any condition of normal operation. This, however, requires the radiated field being sufficiently larger than the image field as to be able to compensate for the repositioning described above. Such an enlarged radiated field results in a higher radiation dose, even though not the entire radiation dose is used for capturing the image and is even not required therefor.

In the scenario shown in FIG. 2, a detector unit 30 is shown with a radiated field 34 and an image field 32 being located within the radiated field 34. The image field is misaligned towards the upper left corner of the radiated field. In other words, the distance between the image field and the upper transversal edge 32A of the radiated field is smaller than the distance between the image field and the lower transversal edge 32B. The same applies to the distance to the lateral edges 32C, 32D: the image field is located closer to the left lateral edge 32C as compared to the right lateral edge 32D. The control unit is configured to determine this lateral and transversal misalignment in the lateral direction 36 and transversal direction 38 depending on the orientation and/or position of the beam source and detector unit and to apply a correction factor to the position of the image field 32 so that it is shifted along the lateral direction 36 and transversal direction 38. This repositioning is preferably done such that the image field is located in the center of the radiated field such that the width of a boundary region of the radiated field going beyond the image field is substantially the same at the two lateral margins and the two transversal margins, respectively.

It should be noted that a rotational misalignment may be compensated for in a similar manner as described with reference to this linear shifting or moving of the image field within the radiated field. For example, the image field may be misaligned by a clockwise or counterclockwise rotational displacement within the radiated field and a corresponding correction factor may be applied to the image field as to compensate for this undesired rotation.

As to reduce the radiation dose, the size of the redundant and unnecessary boundaries of the radiated field are shrunk or minimized by repositioning the image field 32 within the radiated field 34 and reducing the size of the radiated field 34, for example by reducing the cross-section of the opening 42 of the beam limiting unit 40.

The detector unit 30 may comprise multiple receiving units which generate image data as a result of the characteristics of the incoming beam at the respective receiving units. The receiving units may also be referred to as pixels.

The image field 32 may be a region upon the surface of the detector unit 30 and may, in particular, be an area of interest which defines a region of an object of which an image is taken. In other words, the image field may be dynamically adapted and adjusted to define a region of the object, of which region an operator of the imaging system wants to capture an image.

Depending on the position and size of the image field, the beam limiting unit must allow an according beam to pass so that an appropriate region of the detector unit is radiated. However, due to manufacturing tolerances and component tolerances and/or as a result of the position and orientation of the imaging system, the radiated field may need to be larger than the desired imaging field. Further, the imaging field may be misaligned within the radiated field and in order to avoid cutting the image at one or two edges, the radiated field may also be required to be larger.

The imaging system as described herein may help reducing the overall radiation dose and/or beam cross-sectional area for taking an image. A correction factor for the position of the image field within the radiated field is considered and applied so that the overall size of the radiated field may be reduced and adapted to the image field. Subsequently, the size of the radiated field is downsized. Repositioning of the image field within the radiated field may be a shifting or any other movement operation, for example based on a lookup table or a model-based correction. The model-based correction may be done by identifying a model and by inserting the position into the model such that the model determines the correction as an alternative to a lookup table.

The radiated field is downsized. The new opening size of the beam limiting unit may be stored in the memory unit and may be assigned to the orientation of the imaging system. By doing so, the radiation dose is reduced and a higher share of the entire radiation dose is used for the image.

As can be derived from FIG. 2 and expressed in geometrical terms, the ratio of the size of the image field 32 with respect to the size of the radiated field 34 is increased and the overhead, i.e., the width of the margins of the radiated field not required for capturing the image, is reduced and emission of radiation which is not required for capturing the image is reduced.

It should be noted that the size of the radiated field 32 may also be adapted by moving one or more beam shutters of the beam limiting device. The beam limiting device may comprise four shutters for limiting one of the edges 32A, 32B, 32C, 32D, respectively. As to reduce the margins of the radiated field going beyond the image field, the respective shutters may be moved. For example, in the scenario shown in FIG. 2, the shutter assigned to the right edge 32D and the shutter assigned to the lower edge 32B may be moved towards the center of the radiated field as to, thereby, reduce the width of the overhead at these edges.

Figure 3:
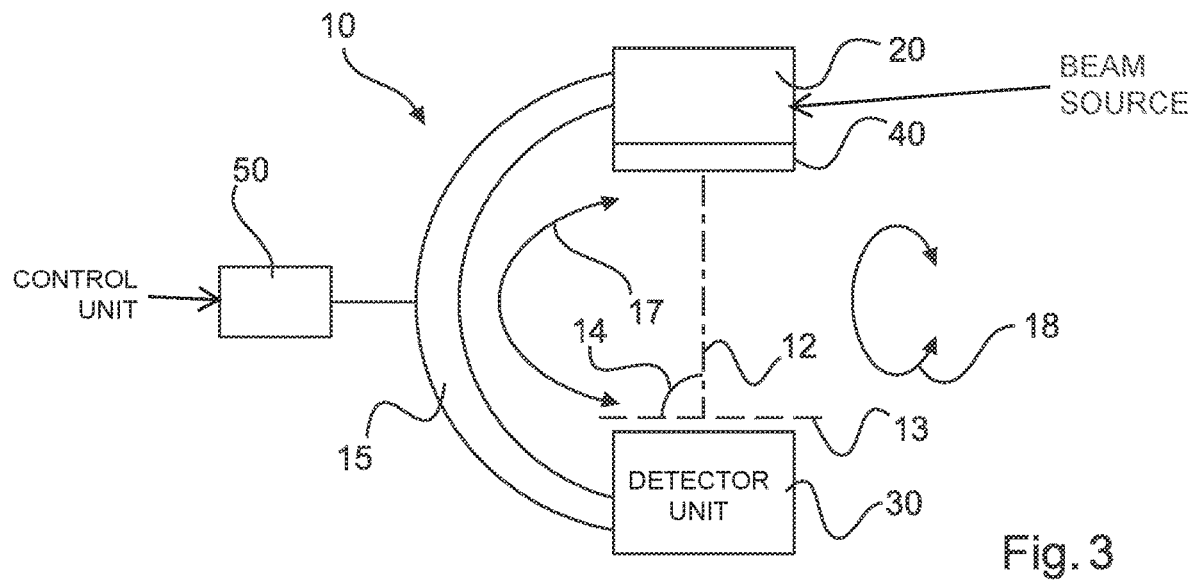
FIG. 3 schematically illustrates an exemplary embodiment of an imaging system.

FIG. 3 schematically illustrates an imaging system 10 as already described with reference to FIG. 1. In Fi. 3, a supporting structure 15 is shown. The supporting structure 15 holds the beam source 20 and the detector unit 30. The beam limiting unit 40 may be located in the same housing as the beam source 20 or may be structurally assigned to the beam source. The supporting structure 15 may be a C-arm, for example. The C-arm may be able to rotate, as indicated by arrow 17. As a result of such a rotational movement, an angle of inclination 14 with respect to a horizontal line 13 which is perpendicular to the force of gravity changes. As a result of the new orientation of the supporting structure together with the beam source and the detector unit, the supporting structure may be subject to bending forces such that the image field is displaced within the radiated field. It should be noted that the supporting structure may rotate such that the beam source 20 and the detector unit 30 are moved out of the drawing layer or into the drawing layer (arrow 18) or such that the beam source 20 and the detector unit 30 are moved to the left and/or right (arrow 17).

Although the embodiment shown in FIG. 3 comprises a supporting structure holding both the beam source and the detector unit, it is noted that in an alternative embodiment, the beam source and the detector unit may be attached to separate supporting structures. For example, the beam source and the detector unit may be suspended to the ceiling or to the floor within a building, respectively.

According to an embodiment of the invention, the control unit is configured to determine an angle of inclination 14 of the imaging system, which angle of inclination corresponds to the orientation of the imaging system.

The angle of inclination 14 defines the inclination of the imaging system and/or of its central axis 12 with respect to a horizontal line 13 in the gravity field of the earth. The horizontal line is arranged orthogonal with respect to the direction of the earth's gravity field.

As a result of a rotation or inclination of the imaging system, the imaging system, and in particular the supporting structure, may slightly bend or deform so that the position of the imaging field in the radiated field is misaligned. This misalignment may be avoided by applying the approach as described herein. Depending on the orientation/inclination of the imaging system, the extent and/or absolute amount of the misalignment may vary. Hence, the correction factor for the position of the image field within the radiated field depends on the orientation of the imaging system.

Figure 4:
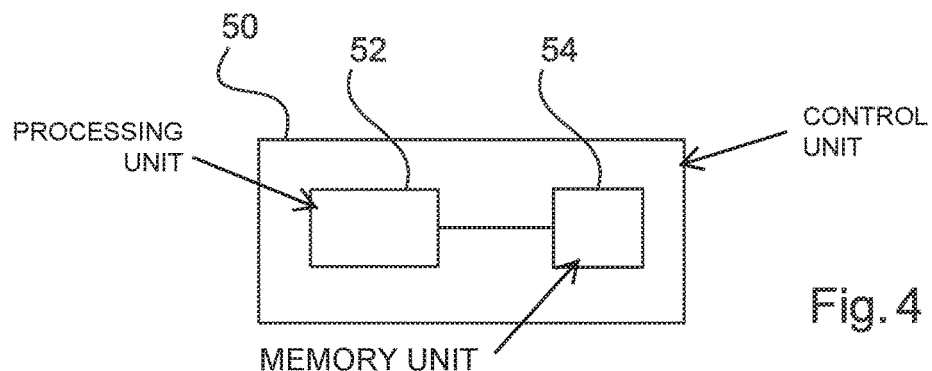
FIG. 4 schematically illustrates an exemplary embodiment of a control unit of an imaging system.

FIG. 4 shows a control unit 50 with a processing unit 52 and a memory unit 54. However, the memory unit 54 may be an external entity with respect to the control unit, too. For example, the memory unit may be a removable component which is connected with the control unit 50 by plugging it into an interface. The control unit may comprise one or more processing units, each of which are configured to execute the same or similar processes in a redundant manner or to, alternatively, execute different processes.

In one embodiment, the control unit may be configured to control the positioning and orientation of the support structure based on predetermined input values, for example given by an operator of the imaging system. The control unit may be configured to determine a correction factor for repositioning and/or orienting the image field within the radiated field based on the predetermined input values. Alternatively or additionally, sensors may be arranged at the imaging system for determining the position and orientation of the supporting structure.

According to an embodiment, the control unit 50 is configured to request the correction factor from the memory unit based on the orientation of the imaging system.

The memory unit may contain a lookup table with correction factor values for multiple positions and orientations of the imaging system. Based on the determined orientation, the predetermined correction factor will be read out of the lookup table and will be applied to the position of the image field such that the desired repositioning is achieved.

According to a further embodiment, the memory unit 54 is configured to store a multitude of correction factors, each of which is assigned to a given orientation of the imaging system.

The correction factors may be determined during a calibration process of the imaging system and may be stored in the memory unit 54. The memory unit may be integral part of the system or may be a removable component, like a memory stick, which may be assigned to an imaging system.

According to a further embodiment, each correction factor contains a lateral component indicating a correction in a lateral direction 36 and a transversal component indicating a correction in a transversal direction 38.

This allows a two-dimensional repositioning in a negative and a positive direction of each dimension, i.e., left/right and up/down in any combination, as shown in FIG. 2. This repositioning may be described with reference to a two-dimensional coordinate system with two axes. One of the lateral or transversal component may also be zero such that there is a repositioning only along one axis, i.e., either lateral or transversal.

The correction factor may also contain a rotational component for indicating a correction of the orientation of the image field, for example by indicating an angle of rotation in the clockwise or counterclockwise direction.

According to a further embodiment, the control unit 50 is configured to reposition the image field 34 within the radiated field 32 such that the image field is spaced apart substantially equidistantly from lateral edges 32C, 32D of the radiated field.

This relates to left-right-centricity, the distance of the image field from the left and right edge is the same, i.e. it is centralized in a lateral direction.

According to a further embodiment, the control unit 50 is configured to reposition the image field 34 within the radiated field 32 such that the image field is spaced apart substantially equidistantly from transversal edges 32A, 32B of the radiated field.

This relates to up-down-centricity, the distance of the image field from the upper and lower edge is the same, i.e. it is centralized in a transversal direction.

The lateral direction is perpendicular to the transversal direction. These directions both extend along the surface of the detection unit.

According to a further embodiment, the control unit is configured to enlarge the image field within the radiated field after repositioning of the image field.

After the repositioning, there are margin areas surrounding the image field so that the radiated field goes beyond the image field at all four edges. In order to avoid radiation which is not used for capturing the image, the image field is enlarged. The ratio of the radiation used for the image in relation to the overall radiation is increased. The new size of the image field may be stored in the memory unit and assigned to the orientation. In other words, for multiple orientation values of the imaging system, the size of the image field is stored additionally to the correction factors referred to above.

According to a further embodiment, the imaging system is an X-ray imaging system and the beam source is an X-ray beam source.

According to a further embodiment, the beam limiting unit is a collimator having an adjustable opening 42 being arranged such that the opening limits the radiated field.

Figure 5:
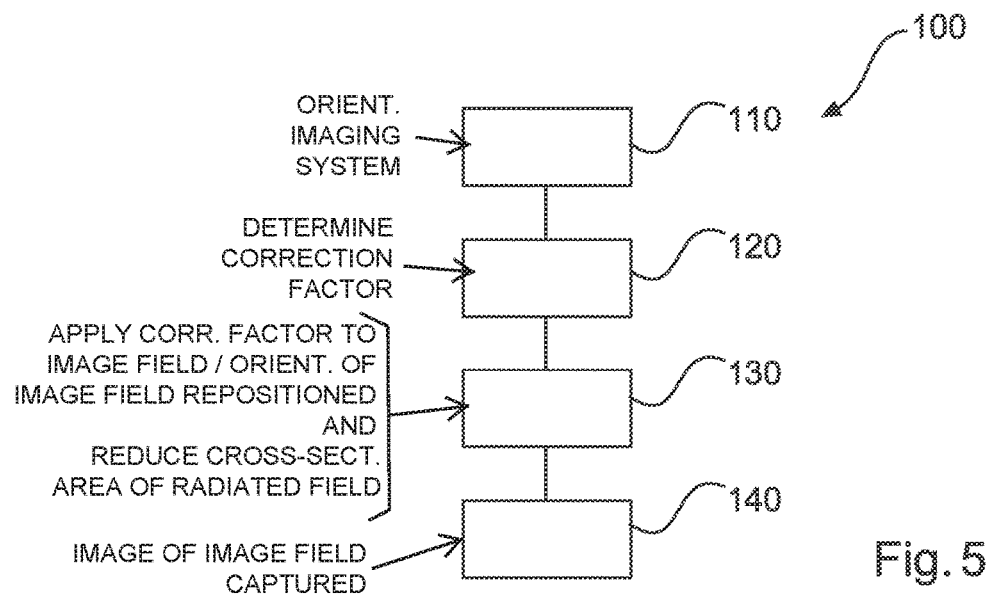
FIG. 5 schematically illustrates a flow chart of a method according to an exemplary embodiment.

According to a further aspect, a method for operating an imaging system is provided. A flow chart of this method is shown in FIG. 5. The method 100 comprises the following steps:

In a first step 110, also indicated as step a), an orientation of the imaging system, in particular of the supporting structure, is determined.

In a second step 120, also indicated as step b), a correction factor to be applied to an image field with respect to a radiated field is determined based on the orientation of the imaging system.

In a third step 130, also indicated as step c), the correction factor is applied to the image field and the orientation of the image field is repositioned and/or adapted with respect to the radiated field in accordance with the correction factor.

In fourth step, also indicated as step d), the cross-sectional area of the radiated field is reduced after repositioning and/or adapting the orientation of the image field with respect to the radiated field. The fourth step is also represented by numeral 130. However, this does not mean that these steps need to be implemented in the same module or that these steps are necessarily implemented and carried out in an immediately succeeding order.

In a fifth step 150, also indicated as step e), an image of the image field is captured.

It is understood that, without repeating here all the explanations, examples, features and/or advantages provided with reference to the imaging system, the method of the invention is intended to be configured to carry out the method steps for which the imaging system is configured to. Thus, all the above examples, explanations, features and/or advantages, although provided previously with reference to the image system, are also intended to be provided in an analogous manner for the method and apply thereto, in particular for the following exemplary embodiments of the method.

The method steps may be carried out in real time, in particular dynamically during taking an image of an object.

According to an embodiment, between steps c) and e), the relative size of the image field with respect to the radiated field is increased.

Either the size of the radiated field is reduced or the size of the image field is enlarged. Both variants result in increasing of the relative size of the image field with respect to the radiated field. When increasing the size of the image field, the size of the radiated field may remain at the same size and when downsizing the radiated field, the image field remains at the same size. However, the image field may be increased while, at the same time, the radiated field may be downsized.

As a result, the ratio of the radiation dose used for the image compared to the total radiation is increased, i.e., a higher share of the total radiation is used for capturing the image.

According to an embodiment, step d) is carried out by controlling a beam limiting unit to reduce a cross-sectional area of a beam projected to a detection unit of the imaging system after repositioning of the image field within the radiated field.

According to an aspect, a computer program element for controlling an imaging system as described above is provided. The computer program element is adapted to perform the method steps of one of the embodiments indicated above when being executed by the control unit of the imaging system described above.

According to an aspect, a computer readable medium is provided, wherein the computer readable medium has stored the program element described above.

In other words, the approach described herein may be summed up as follows with exemplary reference to an X-ray imaging system:

The projected X-ray image on the imaging detector in an X-ray imaging system may be read out by using an automated field limitation correction on the imaging detector. Thus, the imaging system will allow a more accurate and more cost effective field limitation. The automated field limitation makes use of known information of the inaccuracies of the field limitation in the system per position of the C-arc stand. This information may be gathered from a calibration process.

Accurate field limitation of a medical X-ray imaging system is important as such systems need to comply with regulatory aspects stating limits to the amount of misalignment in the field limitation allowed.

The purpose of proper X-ray alignment of an X-ray imaging system is to align the collimated X-ray field to the receptor field for the complete range stand positions that are in use.

It is proposed to use a beam limiting shutter design that allows independent shutter setting at least in two dimensions (i.e. four independent moving shutters). In such design accurate field limitation setting may be done by means of a software calibration algorithm (calibration table) that will allow less rigid and hence much lighter mechanical stand design to be used, hence, providing additional design freedom to the system design used and allowing a lower cost manufacturing.

The approach described herein may allow a more lightweight design of imaging systems. According to the approach presented herein, compensation of image displacement is done by repositioning of the image field. It is therefore not necessary to guarantee a maximum displacement by using a very rigid or stiff (and heavy-weight) structure of the imaging system.

The invention proposes to compensate misalignment (and e.g. sagging) of the imaging system by using a beam limiting design with beam limiting shutters, for example four lateral shutters, that can be moved independently from each other. Each of these lateral shutters may be assigned to an edge of the radiated field.

Accurate field limitation setting is done by means of a calibration algorithm (e.g. a calibration table) that allows independent moving of the shutters in four directions and correcting for misalignment. Hence the sagging of the stand and also the sagging of the shutters in the beam limiting device for all possible positions of use of the imaging system can be actively compensated by moving the shutters according to the calibration table available in the software control of the imaging system.

The above described design will allow less rigid and hence much lighter mechanical stand design to be used hence providing additional design freedom to the system design used and allowing a lower cost manufacturing.

Also when e.g. two imager planes are used there does not need to be a direct mechanical aligned relation between both planes as a software calibration table (different for both planes) can be used, hence relaxing the criteria for mechanical alignment and lowering mechanical design cost.

The main elements of the invention are as follows: a beam limiting device with independently moving beam limiting shutters; a calibration mechanism that will allow evaluation sagging of c-arc and beam limiting shutters; a machine vision based shutter detection mechanism based on analyzing images of the projected beam limiting shutters; a resulting calibration table that will allow real time compensation of beam limiting shutters to allow setting to edge of all possible field formats during its use in the clinical imaging application. Here the calibration table will take into account the orientation of the imaging system. These main elements may be used in any combination with each other in accordance with the embodiments described above.

The effect of the above is a system that even with appreciable sagging in the system will still ensure proper X-ray field limitation during its use. The beam limiting device with independently moving beam limiting shutters may be incorporated in a typical general X-ray system with detector, collimator and X-ray tube mounted for one or more imaging planes.

The stand can have many positions around the patient to deliver the required projections to the medical user (physician) in the medical examination.

Due to the weight of x-ray tube, collimator and detector the c-arc stand needs to be of rigid (hence heavy) construction to avoid possible misalignment due to bending of the stand in the positions needed. The relative effects of misalignment may be larger for smaller image formats used (i.e. 2 mm deflection on an image of 100 mm is a higher percentage share than on an image of 300 mm). For example, it may be required that at least 80% of the X-ray field must be on the imaging area.

Given the proposed solution the c-arc stand can be built less rigid and hence less expensive using an active field limitation compensation mechanism.

The present invention proposes to make use of the known and reproducible deflections of the x-ray beam to actively adapt the receptor field on the x-ray imaging detector such that the mismatch in field limitation is fully minimized in all possible orientations of use of the c-arc stand. Hence a very accurate field limitation mechanism is obtained and dose usage outside the field of view is virtually absent due to the active compensation used.

In common systems, the collimated field of view may be adjusted to the center of the detector image. This adjustment is executed with the geometry in 0 degree rotation and angulation. When the geometry is moved to another position, the C-arc will bend due to the weight of the detector and tube causing a misalignment between the collimated image center and the detector image center. The exact misalignment is known in the geometry software and used to additionally open the collimator such that collimator edges are not in the X-ray image. However, this may allow for a small additional radiated area which is not visible in the image. Also especially in the smaller receptor field sizes the percentage of image field and X-ray field radiated is potentially critical.

Ideally instead of additionally opening the collimator the detector should only read out the collimated area exactly in all possible positions of the geometry. According to the present description, an automated field limitation correction on the imaging detector is proposed. The control unit may determine the amount of misalignment in every position and may translate this into a two-dimensional vector which is used to reposition the image field at the detector unit. During geometry movement, a quasi-real time compensation of e.g. four times per second may be sufficient. When the geometry is stationary, the detector control unit can use the last received value.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to a method whereas other embodiments are described with reference to the apparatus. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single parameter, feature or other element may fulfil the functions of several items re-cited in the claims. The mere fact that certain measures are re-cited in mutually different dependent claims does not

The invention claimed is:

1. An X-ray imaging system, comprising:
an X-ray beam source;
a detector unit;
a beam limiting unit; and
a control unit;
wherein the X-ray beam source is configured to generate a beam and to project the beam onto the detector unit such that a radiated field is projected onto the detector unit;
wherein the beam limiting unit is configured to limit the radiated field;
wherein the detector unit is configured to provide image data as a result of the beam being projected onto the detector unit;
wherein the control unit is configured to provide image data as to generate an image of a desired region of an object being arranged between the X-ray beam source and the detector unit by selecting a predetermined image field of the detector unit;
wherein the control unit is configured to determine a correction factor for a position and/or an orientation of the image field with respect to the radiated field based on an orientation of the X-ray imaging system and to apply the correction factor to the position and/or the orientation of the image field with respect to the radiated field such that the image field is repositioned and/or oriented with respect the radiated field; and
wherein the control unit is configured to control the beam limiting unit as to reduce the cross-sectional area of the beam projected to the detection unit based on the orientation of the X-ray imaging system.

2. The X-ray imaging system of claim 1,
wherein the control unit is configured to determine an angle of inclination of the imaging system and wherein the angle of inclination corresponds to the orientation of the X-ray imaging system.

3. The X-ray imaging system of claim 1,
wherein the X-ray imaging system comprises a memory unit; and
wherein the control unit is configured to request the correction factor from the memory unit based on the orientation of the X-ray imaging system.

4. The X-ray imaging system of claim 3,
wherein the memory unit is configured to store a multitude of correction factors, each of which is assigned to a given orientation of the X-ray imaging system.

5. The X-ray imaging system of claim 1,
wherein each correction factor contains a lateral component indicating a correction in a lateral direction and a transversal component indicating a correction in a transversal direction.

6. The X-ray imaging system of claim 1,
wherein the control unit is configured to reposition the image field within the radiated field such that the image field is spaced apart substantially equidistantly from lateral edges of the radiated field.

7. The X-ray imaging system of claim 6,
wherein the control unit is configured to reposition the image field within the radiated field such that the image field is spaced apart substantially equidistantly from transversal edges of the radiated field.

8. The X-ray imaging system of claim 6,
wherein the control unit is configured to enlarge the image field within the radiated field after repositioning of the image field.

9. The X-ray imaging system of claim 1,
wherein the beam limiting unit is a collimator having an adjustable opening being arranged such that the opening limits the radiated field.

10. A method for operating an X-ray imaging system, comprising the following steps:
a) determining an orientation of the X-ray imaging system;
b) determining a correction factor to be applied to an image field with respect to a radiated field based on the orientation of the X-ray imaging system;
c) applying the correction factor to the image field and repositioning and/or adapting the orientation of the image field with respect to the radiated field;
d) reducing the cross-sectional area of the radiated field unit based on the orientation of the X-ray imaging system; and
e) capturing an image of the image field.

11. The method of claim 10,
wherein between steps c) and e), the relative size of the image field with respect to the radiated field is increased.

12. The method of claim 10,
wherein step d) is carried out by controlling a beam limiting unit to reduce a cross-sectional area of a beam projected to a detection unit of the X-ray imaging system based on the orientation of the X-ray imaging system.

13. A computer program element for controlling an X-ray imaging system according to the X-ray imaging system comprising an X-ray beam source; a detector under; a beam limiting unit and a control unit, which, when being executed by the control unit, is configured to perform the method steps of claim 10.

14. A non-transitory computer-readable medium having stored the program element of claim 13.

* * * * *